United States Patent [19]

Avakian

[11] 4,059,020
[45] Nov. 22, 1977

[54] FILTER FOR MICROPIPETTES
[75] Inventor: Souren Avakian, Westport, Conn.
[73] Assignee: Centaur Chemical Co., Stamford, Conn.
[21] Appl. No.: 721,874
[22] Filed: Sept. 9, 1976
[51] Int. Cl.² .............................................. B01L 3/02
[52] U.S. Cl. ................................. 73/425.4 P; 23/292; 210/482
[58] Field of Search .................. 73/425.4 P, 425.6; 23/253, 259, 292; 210/464, 466, 473, 482

[56] References Cited

U.S. PATENT DOCUMENTS

| | | | |
|---|---|---|---|
| 3,449,081 | 6/1969 | Hughes | 73/425.6 |
| 3,985,032 | 10/1976 | Avakian | 73/425.4 P |

FOREIGN PATENT DOCUMENTS 2,979  7/1931  Australia .............................. 210/468

*Primary Examiner*—S. Clement Swisher
*Attorney, Agent, or Firm*—Buckles and Bramblett

[57] ABSTRACT

A disposable two part filter assembly for use on the detachable tip of a laboratory pipette. It comprises a body member with an opening shaped and sized to engage the tip. Such body members may be provided for a wide range of tip sizes and shapes. Inserted within each of the body members is a filter element. The filter elements have essentially the same size and shape but may differ as to material and porosity.

5 Claims, 4 Drawing Figures

U.S. Patent      Nov. 22, 1977      4,059,020
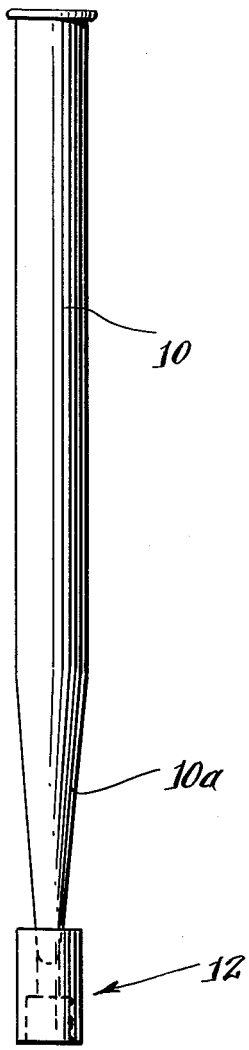
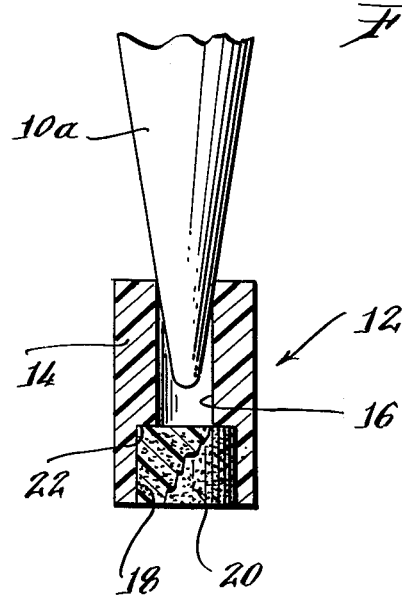
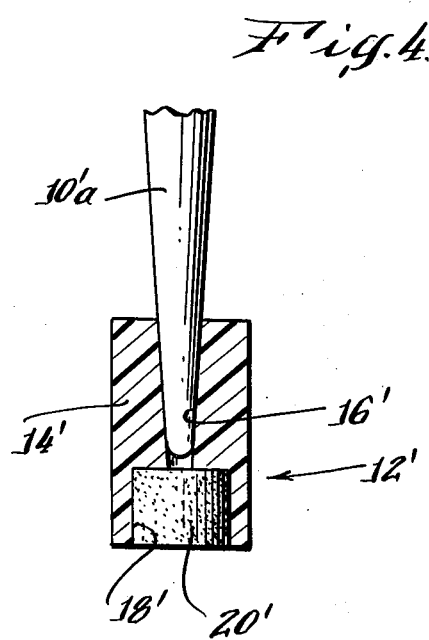
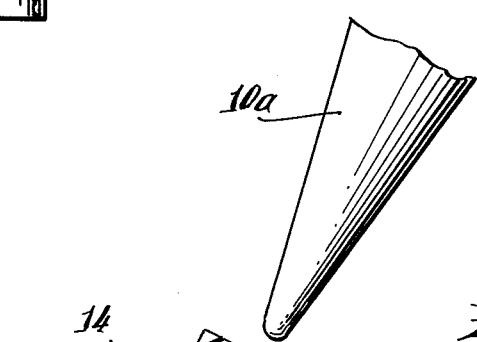
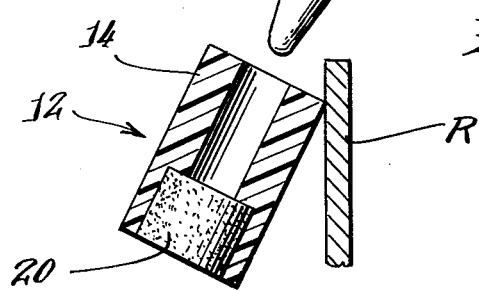

FILTER FOR MICROPIPETTES

BACKGROUND OF THE INVENTION

In my co-pending U.S. application Ser. No. 631,847 filed Nov. 13, 1975 for "Micropipette Filter Tips" there is disclosed a filter for use with the disposable plastic tips of micropipettes. The filter is of porous plastic or metal and is designed to engage the tip while the liquid is being sampled and simultaneously filtered. Thereafter the filter may be removed and the filtered liquid discharged. In one of the embodiments disclosed in such application, the filter is shown in the form of a sphere having a conical recess for frictionally engaging the tip of the micropipette.

Filters of the type covered by the aforesaid pending application are useful laboratory tools. However, one potential disadvantage arises from the fact that the filter itself provides the frictional engagement retaining it on the tip. This means that if a number of tips are employed having different sizes and shapes, there must be an equally large selection of filters, even though the filtering material may be the same. Furthermore, if a selection of filter materials is desired, it would be necessary to make the filters of each material in a sufficiently large variety to fit all the various tips with which they are apt to be used. Accordingly, it is a primary object of the present invention to provide filter assemblies comprising a body member having a size and shape to engage a specific tip and a standardized filter insert which may be interchangeably associated with all such holders. Other objects, features, and advantages will become apparent from the following description and appended claims.

SUMMARY OF THE INVENTION

A filter apparatus for use with a liquid sampling pipette of the type having a detachable tip member in the form of a truncated hollow cone defining an axial reservoir therethrough and an opening at the tip end communicating with the reservoir to receive a liquid sample. The apparatus comprises a liquid impervious body member which defines a liquid passage therethrough, the passage being dimensioned to frictionally engage the tip of the pipette. A porous filter is retained by the body member in alignment with the liquid passage.

BRIEF DESCRIPTION OF THE DRAWING

FIG. 1 is an elevational view of a filter assembly in accordance with the invention positioned on a pipette tip;

FIG. 2 is an enlarged view in partial cross section of the filter of FIG. 1;

FIG. 3 is an enlarged illustration, partially in cross section, showing the removal of the filter assembly of FIGS. 1 and 2 from the tip; and, FIG. 4 is an illustration showing, in cross section, a modified form of the filter assembly of FIGS. 1–3.

DESCRIPTION OF THE PREFERRED EMBODIMENT

With particular reference to FIG. 1, there is illustrated a plastic tip member 10 of the type employed with pipettes for sampling liquids. It includes a conical tip 10a which terminates in an opening for receiving the sample liquid therein. FIG. 1 illustrates the tip 10 with the filter assembly 12 of the invention mounted thereon.

Filter assembly 12 is shown in more detail in FIG. 2. It comprises a cylindrical body 14 formed of a plastic which is non-reactive with the material to be sampled. The body 14 defines a central, cylindrical passage 16 which communicates with an enlarged recess 18 at the end to thereby form an interior annular shoulder 22. Mounted within the recess 18 and against the shoulder 22 is a filter disc 20 which may be made of porous plastic, metal, or other suitable material.

In FIGS. 1 and 2, the filter assembly 12 is shown frictionally engaging the conical portion 10a of the tip 10 and in this position it is dipped into the liquid to be sampled. Upon actuation of the pipette, sample fluid is drawn through the filter 20 and into the tip, undergoing filtration in the process. Thereafter, the filter assembly is removed, as by engagement with the rim R of a receptacle as shown in FIG. 3. The filtered fluid may thereafter be discharged from the tip by depression of the pipette plunger.

In order to accommodate tips of various sizes and shapes, various body members may be supplied. One modification, for example, is shown in FIG. 4 where assembly 12' is illustrated comprising a cylindrical body member 14' which has a conically tapered internal passage 16'. The filter disc 20' is shown as having the same physical dimensions as disc 20. Its porosity and the material from which it is made may differ.

It will be apparent from the foregoing description that this invention makes it possible to supply filter assemblies for accommodating pipette tips of varying sizes and shapes without requiring changes in the size and shape of the filter elements themselves. The same construction also makes it possible to insert filters of different materials and porosity into identical or differing holders. Accordingly, a number of combinations may be achieved which were not possible in the prior art construction. It will also be apparent that the filter assemblies may be assembled by the manufacturer or by the end user as desired.

Other variations and modifications of this invention will also be apparent to those skilled in the art. Accordingly, the foregoing description is to be construed as illustrative only, rather than limiting. This invention is limited only by the scope of the following claims.

What is claimed is:

1. Filter apparatus for use with a liquid sampling pipette having a detachable tip member in the form of a truncated hollow cone defining an axial reservoir therethrough and an opening defined by the truncated tip and communicating with the reservoir to receive a liquid sample therethrough which comprises: a liquid impervious body member defining a liquid passage therethrough, said passage being dimensioned to frictionally solely by friction engage said tip; and a porous filter plug retained by said body member in alignment with said liquid passage.

2. The apparatus of claim 1 wherein said passage includes a recessed portion enclosing said filter plug.

3. The apparatus of claim 2 wherein said recessed portion and said filter plug are substantially cylindrical.

4. The apparatus of claim 1 wherein said filter plug is porous plastic.

5. The apparatus of claim 1 wherein said filter plug is porous metal.

* * * * *

UNITED STATES PATENT OFFICE
CERTIFICATE OF CORRECTION

Patent No. 4,059,020             Dated November 22, 1977

Inventor(s)   SOUREN AVAKIAN

It is certified that error appears in the above-identified patent and that said Letters Patent are hereby corrected as shown below:

Column 2, line 54, delete "frictionally"; line 55, delete "solely by friction engage said tip" and insert therefor --engage said tip solely by friction--.

Signed and Sealed this

Fourteenth Day of March 1978

[SEAL]

Attest:

RUTH C. MASON
Attesting Officer

LUTRELLE F. PARKER
Acting Commissioner of Patents and Trademarks